US012648752B2

(12) United States Patent
Bonnefous et al.

(10) Patent No.: US 12,648,752 B2
(45) Date of Patent: Jun. 9, 2026

(54) NONINVASIVE MEASUREMENT OF LEFT VENTRICULAR COMPLIANCE

(71) Applicant: KONINKLIJKE PHILIPS N.V., Eindhoven (NL)

(72) Inventors: Odile Bonnefous, Rueil-Malmaison (FR); Francois Guy Gerard Marie Vignon, Andover, MA (US); Seyedali Sadeghi, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 169 days.

(21) Appl. No.: 18/564,652

(22) PCT Filed: May 20, 2022

(86) PCT No.: PCT/EP2022/063723
§ 371 (c)(1),
(2) Date: Nov. 28, 2023

(87) PCT Pub. No.: WO2022/248355
PCT Pub. Date: Dec. 1, 2022

(65) Prior Publication Data
US 2024/0260927 A1     Aug. 8, 2024

(30) Foreign Application Priority Data

May 28, 2021     (EP) ..................................... 21290035

(51) Int. Cl.
*A61B 8/06*          (2006.01)
*A61B 8/00*          (2006.01)
*A61B 8/04*          (2006.01)

(52) U.S. Cl.
CPC ................ *A61B 8/065* (2013.01); *A61B 8/04* (2013.01); *A61B 8/5223* (2013.01)

(58) Field of Classification Search
CPC .......... A61B 8/5223; A61B 8/04; A61B 8/065
See application file for complete search history.

(56) References Cited

U.S. PATENT DOCUMENTS

2003/0114756 A1*  6/2003  Li ........................ G01S 7/52065
                                                        600/437
2007/0016031 A1   1/2007  Mourad et al.
2007/0016037 A1*  1/2007  Houle ...................... A61B 8/06
                                                        600/438
2012/0172727 A1*  7/2012  Hastings .................. A61B 8/06
                                                        600/463

(Continued)

FOREIGN PATENT DOCUMENTS

WO          2020127646 A1     6/2020

OTHER PUBLICATIONS

International Search Report and Written Opinion for PCT/EP2022/063723; Mailing date: Sep. 26, 2022, 8 pages.

(Continued)

*Primary Examiner* — John D Li

(57)          ABSTRACT

A mechanism for performing a non-invasive estimate of left ventricular compliance. A temporal variation of left ventricular volume and a temporal variation of left ventricular pressure are determined by processing ultrasound data of a subject. These two temporal variations are then processed to estimate left ventricular compliance.

15 Claims, 3 Drawing Sheets

(56)        References Cited

U.S. PATENT DOCUMENTS

| | | | |
|---|---|---|---|
| 2013/0245441 A1 * | 9/2013 | Datta | A61B 8/0883 |
| | | | 600/438 |
| 2013/0279294 A1 * | 10/2013 | Angelsen | G01S 7/52042 |
| | | | 367/87 |
| 2016/0228190 A1 | 8/2016 | Georgescu et al. | |

OTHER PUBLICATIONS

Hanowell, L. et al., "Transesophageal echocardiography in the perioperative assessment of intravascular volume", Seminars in Anesthesia, Perioperative Medicine and Pain, 1998, vol. 17, pp. 252-266.
Demaria, A. et al., "Mitral valve early diastolic closing velocity in the echocardiogram: Relation to sequential diastolic flow and ventricular compliance", The American Journal of Cardiology, 1976, vol. 37, Issue 5, pp. 693-700.

\* cited by examiner

NONINVASIVE MEASUREMENT OF LEFT VENTRICULAR COMPLIANCE

CROSS-REFERENCE TO PRIOR APPLICATIONS

This application is the U.S. National Phase application under 35 U.S.C. § 371 of International Application No. PCT/EP2022/063723, filed on May 20, 2022, which claims the benefit of European Patent Application No. 21290035.1, filed on May 28, 2021. These applications are hereby incorporated by reference herein.

FIELD OF THE INVENTION

The present invention relates to the field of heart monitoring, and in particular, to the field of measuring left ventricular compliance of a subject's heart.

BACKGROUND OF THE INVENTION

Left ventricular compliance is a measurement that can be used of an indicator of likelihood of diastolic heart failure. Typically, left ventricular compliance is defined as the differential of a volume-pressure curve (dV/dP) within the left ventricle of the patient's heart during a diastolic phase of the patient's heart. The greater the value of the left ventricular compliance, the less pressure is needed to effect a change in volume within the left ventricle of the subject's heart, meaning that the subject is less susceptible to diastolic heart failure.

Approaches for calculating of left ventricular compliance therefore usually require a pressure reading directly within or near the left ventricle of a subject's heart, which is a highly invasive medical procedure.

It would be desirable to provide a less invasive, and preferably minimally invasive or non-invasive, approach for assessing left ventricular compliance.

One approach in the prior art proposes to measure myocardial stiffness/compliance through direct elastographic measurement. However, although myocardial compliance and ventricular compliance are related, they are not the same; as myocardial compliance is an intrinsic local tissue property whereas ventricular compliance can depend on other factors such as chamber shape.

There is therefore a desire to provide a mechanism for performing accurate determination or prediction of left ventricular compliance.

SUMMARY OF THE INVENTION

The invention is defined by the claims.

According to examples in accordance with an aspect of the invention, there is provided a computer-implemented method for performing non-invasive estimation of left ventricular compliance for a subject.

The computer-implemented method comprises: obtaining ultrasound data of the subject's heart, wherein the ultrasound data was captured over a time period comprising at least a portion of a cardiac cycle of the heart and comprises velocity data along a direction of mitral inflow; determining, by processing the velocity data, a velocity component along the direction of mitral inflow of the heart over the time period; determining a temporal variation of the left ventricular pressure from the determined velocity component by processing the velocity component using a physical model; determining, by processing the obtained ultrasound data, a temporal variation of the left ventricle volume; and estimating the left ventricular compliance by processing the determined temporal variation of the left ventricle volume and the determined temporal variation of the left ventricular pressure.

The present disclosure therefore provides an approach for estimating (a value or function of) left ventricular compliance by processing only ultrasound data. Thus, a non-invasive procedure is proposed for predicting left ventricular compliance. A non-invasive procedure reduces a likelihood of adverse effects (e.g. reduces a risk of infection), improves a speed of obtaining a measure of left ventricular compliance (e.g. as no surgical intervention is required) and/or can be performed by fewer or less experienced clinicians than an invasive mechanism.

The present disclosure effectively proposes to determine a time differential ("temporal variation") of left ventricular pressure and a time differential ("temporal variation") of left ventricular volume. These two features are then processed to predict a left ventricular compliance.

It is herein recognized that a temporal variation of left ventricular pressure and a temporal variation of left ventricular volume can both be obtained through appropriate processing of ultrasound data (of a subject's heart). Moreover, it is recognized that these two features can be processed to calculate left ventricular compliance. Thus, an underlying recognition of the present disclosure is that an approach for determining left ventricular compliance can be (re)cast or formulated into steps that can be executed by appropriate processing of ultrasound data (alone).

The step of estimating the left ventricular compliance may comprise determining the ratio between the temporal variation of the left ventricle volume and the temporal variation of the left ventricular pressure. In other words, the left ventricular compliance may be estimated by dividing the temporal variation of the left ventricle volume by the temporal variation of the left ventricular pressure.

The step of determining the temporal variation of the left ventricular pressure may comprise processing the velocity component using the Navier-Stokes equation to determine the temporal variation of the left ventricular pressures. The Navier-Stokes equation can thereby act as the physical model, and provide a mechanism for deriving a temporal variation of left ventricular pressure from one or more velocity components of velocity data of the ultrasound data.

The step of determining the temporal variation of the left ventricle volume may comprise determining the temporal variation of the left ventricle volume by processing the velocity component. It is recognized that a temporal variation of left ventricular volume is responsive to (i.e. changes in response to changes of) a velocity of blood entering the left ventricle (i.e. via the mitral valve). This means it is possible to calculate, determine or predict the temporal variation of the left ventricle volume based on a velocity component of blood flow through the mitral valve.

The step of determining the temporal variation of the left ventricle volume may comprise multiplying the velocity component by a surface area value, the surface area value representing a surface area size of the mitral annulus of the subject's heart.

Optionally, the computer-implemented method further comprises a step of determining the surface area value, said step comprising: determining, by processing the ultrasound data, a first volume of the left ventricle, of the subject's heart wherein the first volume is a volume of the left ventricle of the subject's heart at a first point during the portion of the cardiac cycle of the subject's heart; determining, by processing the ultrasound data, a second volume of the left ventricle, of the subject's heart wherein the second volume is a volume of the left ventricle of the subject's heart at a second, later point during the portion of the cardiac cycle of the subject's heart; determining the difference between the second volume and the first volume; determining the integral of the velocity component between the first point and the second point during the portion of the cardiac cycle of the subject's heart; and determining the ratio between the difference between the second volume and the first volume and the integral, to thereby calculate the surface area value.

In some embodiments, the computer-implemented method is adapted wherein: the ultrasound data was captured over a time period comprising at least a portion of a cardiac cycle of the heart that includes an end-systolic phase of the cardiac cycle and an end-diastolic phase of the cardiac cycle, the first point is a point in the end-systolic phase of the cardiac cycle; and the second point is a point in the end-diastolic phase of the cardiac cycle.

In other examples, the surface area value may be predetermined. For instance, the surface area value may be a value that represents a (global) average size for a surface area of the mitral valve.

In some examples, the ultrasound data is ultrasound data that was captured over a time period comprising at least a portion of a cardiac cycle of the heart that includes an end-diastolic phase of the cardiac cycle; the temporal variation of the left ventricle volume is a temporal variation of the left ventricle volume during the end-diastolic phase of the cardiac cycle; and the temporal variation of the left ventricular pressure is a temporal variation of the left ventricular pressure during the end-diastolic phase of the cardiac cycle.

The computer-implemented method may be adapted wherein: the step of determining a temporal variation of the left ventricle volume comprises processing the ultrasound data to determine a first set of measurements, each measurement in the first set of measurements representing the temporal variation of the left ventricle volume at a different, respective time point during the time period over which the ultrasound data was captured; the step of determining a temporal variation of the left ventricular pressure comprises processing the at least one velocity component using a physical model to determine a second set of measurements, each measurement in the second set of measurements corresponding to a measurement of the first set of measurements and representing the temporal variation of the left ventricular pressure at the same time point as the corresponding measurement of the first set of measurements; and the step of estimating the left ventricular compliance comprises processing the first set of measurements and the second set of measurements to estimate the left ventricular compliance.

In some examples, the step of estimating the left ventricular compliance comprises: multiplying each measurement of the first set of measurements by the corresponding measurement in the second set of measurements, to produce a multiplied set of measurements; averaging the multiplied set of measurements to produce an averaged multiplied measurement; squaring each measurement of the second set of measurements to produce a squared set of measurements; averaging the squared set of measurements to produce an averaged squared measurement; and estimating the left ventricular compliance by determining a ratio between the averaged multiplied measurement and the averaged squared measurement.

There is also proposed a computer program product comprising computer program code means which, when executed on a computing device having a processing system, cause the processing system to perform all of the steps of the method herein described. The computer program product may be a (non-transitory) computer storage medium.

There is also proposed a processing arrangement for performing estimation of left ventricular compliance for a subject.

The processing arrangement is configured to: obtain ultrasound data of the subject's heart, wherein the ultrasound data was captured over a time period comprising at least a portion of a cardiac cycle of the heart and comprises velocity along a direction of mitral inflow; determine, by processing the velocity, a velocity component along the direction of mitral inflow of the heart over the time period; determine, by processing the obtained ultrasound data, a temporal variation of the left ventricle volume; determine a temporal variation of the left ventricular pressure from the determined velocity component by processing the velocity component using a physical model; and estimate the left ventricular compliance by processing the determined temporal variation of the left ventricle volume and the determined temporal variation of the left ventricular pressure.

There is also proposed an imaging system comprising: the processing arrangement previously described; and an ultrasound system configured to capture ultrasound data of the subject's heart and provide the ultrasound data to the processing arrangement.

There is also proposed a processing system comprising: the processing arrangement or the imaging system; and an output interface configured to provide a user-perceptible output responsive to the left ventricular compliance estimated by the processing arrangement.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
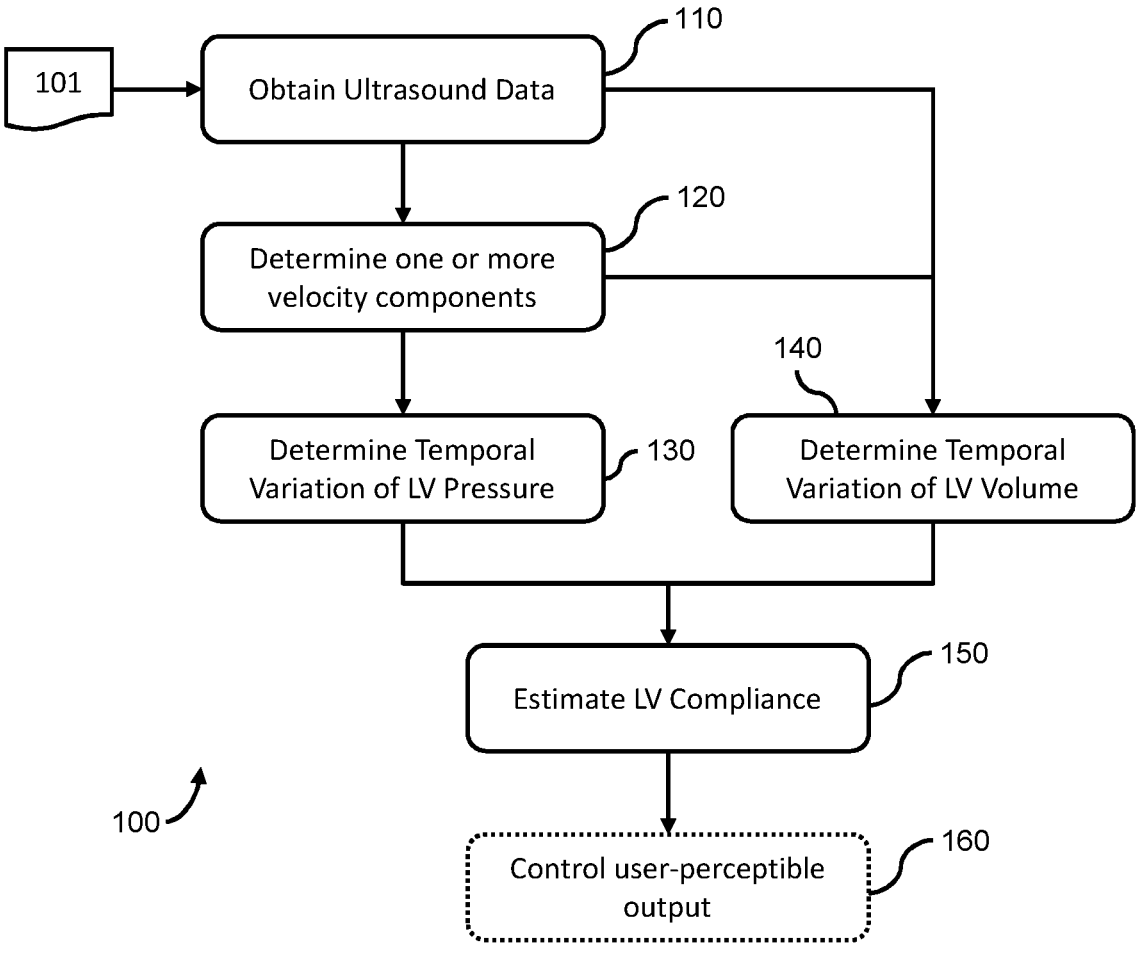
FIG. 1 is a flowchart illustrating a method according to an embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a mechanism for performing a (non-invasive) estimate of left ventricular compliance. A temporal variation of left ventricular volume and a temporal variation of left ventricular pressure are determined by processing ultrasound data of a subject. These two temporal variations are then processed to estimate left ventricular compliance.

Embodiments are based on the realization that a measure for left ventricular compliance of a subject can be derived from measurements that can be estimated from ultrasound data of the subject's heart. In particular, appropriate processing of ultrasound data facilitates determination of a measurement of left ventricular compliance.

Accurate estimation or calculation of left ventricular compliance has an important diagnosis and prognostic value in heart failure with preserved ejection fraction (a.k.a. "diastolic" heart failure). It would represent a direct estimate of compliance as opposed to the surrogate measurements now used in clinical practice.

FIG. 1 is a flowchart illustrating a (computer-implemented) method 100 according to an embodiment. The illustrated method 100 is non-invasive, e.g. as it makes use of ultrasound data alone.

The method generates a predicted left ventricular compliance, which may be in the form of a function (e.g. a function of time) and/or one or more discrete values/measurements of a left ventricular compliance.

The method 100 comprises a step 110 of obtaining ultrasound data 101 of the subject's heart. The ultrasound data is data that has been captured over a time period comprising at least a portion of a cardiac cycle of the heart.

The ultrasound data may be obtained, for example, directly from an ultrasound imaging device or from a memory (e.g. that stores data generated by the ultrasound imaging device).

The ultrasound data comprises velocity data along a direction of mitral inflow. Velocity data, or "blood velocity data", is any ultrasound data that can be processed to identify a velocity of blood flow in at least the direction of mitral inflow (i.e. blood flow through the mitral valve). Suitable examples of velocity data includes (color) M-mode acquisition data, i.e. a (color) M-mode trace, and/or other Doppler ultrasound data.

The method 100 performs a step 120 of processing the velocity data to determine one or more velocity components along the direction of mitral inflow of the heart over the time period. Suitable velocity components include an inertial component and a convective component. A velocity component may be a velocity component as a function of (at least) time.

By way of example, velocity data (of the ultrasound data 101) may provide a blood velocity as a function of time and distance, i.e. a blood velocity function $v_r(r,t)$, where $v_r$ represents a measure of blood velocity, r represents a distance in a direction along the mitral valve from the left atrium to the left ventricle and t represents time. As a value for r increases, so a position between the left atrium and the left ventricle changes. The blood velocity function may be a standard or conventional output of an (color) M-mode trace of the heart of the subject, as would be readily appreciated by the skilled person. Thus, mechanisms for generating a blood velocity function are well established in the art.

Processing the velocity data, in step 120, to determine one or more velocity components may comprise calculating an internal component $$\left(-\rho\frac{\partial v_r}{\partial t}\right),$$

or temporal derivative component, and/or a convective component $$\left(-\rho v_r\frac{\partial v_r}{\partial_r}\right),$$

or distance derivate component, of the velocity data. ρ is density, and is assumed to be known or a predetermined value.

The skilled person will appreciate that different values of r represent different positions along the direction of mitral inflow. Different anatomical elements may be associated with different values of r, representing the position of the anatomical element along the direction of mitral inflow. An r value for a particular anatomical element (such as the mitral valve) can be identified, e.g. by segmenting the ultrasound data to identify the anatomical element and identifying the corresponding r value for the position of the ultrasound data. This can be achieved because the positional relationship between positions in the ultrasound data and corresponding position along the r scale is predetermined or derivable (as the ultrasound data will contain a representation of the direction along the mitral valve).

The method 100 then moves to a step 130 of determining a temporal variation of the left ventricular pressure (∂P/∂t) from the determined velocity component (in step 120) by processing the velocity component using a physical model.

A suitable physical model for use in step 130 is provided by the Navier Stokes equation as follows:

$$\frac{\partial P}{\partial r}(r,t) = -\rho\left(\frac{\partial v_r}{\partial t}(r,t) + v_r\frac{\partial v_r}{\partial r}(r,t)\right) \tag{1}$$

This equation makes use of the internal component and convective component of the velocity data previously described. However, the skilled person would readily appreciate other approaches and physical models that could be used to determine the temporal variation of the left ventricular pressure.

The Navier Stokes equation outputs a distance variation of the pressure $$\frac{\partial p}{\partial r}(r,t)$$

as a function of distance and time, i.e. a pressure gradient. This pressure gradient may then be integrated (from the position of the atrium to the position of the ventricle on the r-scale) to obtain the left ventricular pressure as a function of time (i.e. to obtain P(t)). The position of the atrium and the ventricle on the r-scale may be readily identifiable through appropriate processing of the velocity data and/or ultrasound data.

Obtaining the temporal variation of the left ventricle function can then be carried out by differentiating the left ventricular pressure as a function of time with respect to time, i.e. to calculate ∂P/∂t.

The method 100 also performs a step 140 of processing the ultrasound data to determine a temporal variation of the left ventricle volume (i.e. $\partial V/\partial t$). This can be performed, for instance, by processing image data (e.g. 2D or 3D pixel/voxel data) to determine a difference or a change in volume at a particular point in time.

For instance, the ultrasound data may comprise pixel/voxel data as a function of time. This pixel/voxel data could be segmented, e.g. using an automated segmentation approach, to determine a volume of the left ventricle as a function of time. This function could then be differentiated to extract a temporal variation of the left ventricle volume as a function of time.

In particular, each frame of the pixel/voxel data may be segmented to identify a region representing the left ventricle, i.e. the predicted bounds of the left ventricle. The volume of the left ventricle can be determined based on the predicted bounds of the left ventricle for each frame. These discrete volume values can be converted into a function, e.g. a best fit function, to thereby produce the predicted volume of the left ventricle as a function of time. This produced function may then be differentiated to generate the temporal variation of the left ventricle volume as a function of time.

An alternative approach could be to process the velocity data of the ultrasound data, e.g. the color M-mode trace. Assuming that blood flow goes through a constant surface area S at the mitral annulus, then $\partial V/\partial t = v_r(t) \cdot S$. The function $v_r(t)$, a function of blood velocity as a function of time, may be derived from the blood velocity (in the velocity data) as a function of time and position: $v_r(r,t)$, where the value for r is selected to identify a predicted/relative position of the mitral annulus in the mitral valve, e.g. is a predetermined value. The value for r may be selected based on a known position of the mitral annulus with respect to r, e.g. based on an assessment of the ultrasound data and/or velocity data. In one example, an r value may be selected that provides the maximum value $v_r(r,t)$ (for any t). This example reflects an expectation that the maximum blood velocity will occur at the mitral annulus (e.g. where the cross-sectional area is smallest).

Thus, determining the temporal variation of the left ventricle volume may comprise multiplying the velocity component by a surface area value S, the surface area value representing a surface area size of the mitral annulus of the subject's heart.

The value for S could be assumed to be constant, e.g. a predetermined or pre-estimated value. For instance, the value for S could be an average value (e.g. a global average or an average from amongst similar subjects).

In other examples, it may be possible to calibrate for S, e.g. calculate a subject-specific value for S. This can be performed by looking at the end-systolic and end-diastolic volume, e.g. as measured from voxel data of the heart obtained at the end of the systolic phase and at the end of the diastolic phase. The time-integral of $\partial V/\partial t = v(t) \cdot S$ over the diastolic phase (i.e. from the end of the systolic phase to the end of the diastolic phase) should be equal to the volume increase over the diastolic phase.

Thus, more generally, the method may comprise a step of determining the surface area value S. This step may comprise: determining, by processing the ultrasound data, a first volume of the left ventricle, of the subject's heart wherein the first volume is a volume of the left ventricle of the subject's heart at a first point during the portion of the cardiac cycle of the subject's heart (e.g. at the end of the systolic phase); determining, by processing the ultrasound data, a second volume of the left ventricle, of the subject's heart wherein the second volume is a volume of the left ventricle of the subject's heart at a second, later point during the portion of the cardiac cycle of the subject's heart (e.g. at the end of the diastolic phase); determining the difference between the second volume and the first volume; determining the integral of the velocity component between the first point and the second point during the portion of the cardiac cycle of the subject's heart; and determining the ratio between the difference between the second volume and the first volume and the integral, to thereby calculate the surface area value.

One advantage of processing velocity data using such approaches is the synchronous measurements of volume and pressure from data obtained during the same cardiac cycle, and where the same data is used (i.e. data sampled at the same time points).

The method 100 then performs a step 150 of estimating the left ventricular compliance by processing the determined temporal variation of the left ventricle volume and the determined temporal variation of the left ventricular pressure. In particular, step 150 may comprise determining one or more values of left ventricular compliance by processing the determined temporal variation of the left ventricular volume and the temporal variation of the left ventricular pressure.

In one example, step 150 comprises determining the ratio between the temporal variation of the left ventricle volume and the temporal variation of the left ventricular pressure.

Thus, where $\kappa$ represents left ventricular compliance, it can be calculated using the following equation:

$$\kappa(t) = \frac{\dfrac{\partial V}{\partial t}(t)}{\dfrac{\partial P}{\partial t}(t)} \tag{2}$$

A specific value or sample for left ventricular compliance could be calculated for each of a plurality of different points in time (e.g. by selecting an appropriate time value for t).

In some examples, an average left ventricular compliance could be calculated by averaging multiple values for left ventricular compliance that have been calculated using equation (2) for different values of t. The values of t may be selected so that they all fall within a predetermined phase of the motion of the subject's heart, e.g. all fall within the diastolic phase of the subject's heart movement and/or all within a single cardiac cycle of the subject's heart. The values of t may be evenly distributed.

In some other examples, the step of estimating the left ventricular compliance may comprise using a first set of measurements/samples (of the temporal variation of the left ventricle volume) and a second set of measurements/samples (of the temporal variation of the left ventricle pressure). Each measurement in the first/second set of measurements represents a measurement at a particular point in time (e.g. for a different value of t).

Each measurement may represent a measurement at a particular point in time t, e.g. within a predetermined phase of the motion of the subject's heart. Each measurement in the first set of measurement corresponds to a measurement in the second set of measurements, e.g. measurement representing a same point in time. Thus, the total number of measurements in the first set is identical to the total number of measurements in the second set.

The first and second sets of measurements may be associated with a particular period of time, e.g. part of a single cardiac cycle of the subject, such as part of the end-diastolic phase of the subject. In this scenario, all measurements in the first/second set are measurements obtained for values of t that fall within this particular period of time. The values of t (for the measurements of the first/second set of measurements) may be selected so that they all fall within a predetermined phase of the motion of the subject's heart, e.g. all fall within the diastolic phase of the subject's heart movement and/or all within a single cardiac cycle of the subject's heart. The values of t may be evenly distributed.

A value for the left ventricular compliance $\kappa$ may then be calculated using the following equation:

$$\kappa = \frac{E\left(\frac{\partial V}{\partial t}(t) \cdot \frac{\partial P}{\partial t}(t)\right)}{E\left(\left|\frac{\partial P}{\partial t}(t)\right|^2\right)} \quad (3)$$

where E(f(t)) is an averaging function, which is calculated by the following equation $$E(f(t)) = \frac{\sum_{t=i}^{t=j} f(t)}{n} \quad (4)$$

where f(t) represents some arbitrary function of t $$\left(\text{e.g. } \frac{\partial V}{\partial t}(t) \cdot \frac{\partial P}{\partial t}(t) \text{ or } \left|\frac{\partial P}{\partial t}(t)\right|^2\right),$$

i represents a first point in time, j represents some later point in time and n represents the total number of values for f(t) obtained. In particular, i represents a first measurement in the first/second set of measurements and j represents a last measurement in the first/second set of measurements.

Thus, the value for $$E\left(\frac{\partial V}{\partial t}(t) \cdot \frac{\partial P}{\partial t}(t)\right)$$

in equation (3) is calculated by determining, for each measurement in the first set of measurements, the product of said measurement and the corresponding measurement of the second set of measurements. The products produced in this step are then summed, and the summed products are divided by the total number of products (or the total number of measurements in the first/second set of measurements).

The skilled person would readily appreciate how this understanding can be extended to the other function in equation (3), and how to adopt the method accordingly.

In an alternative, but less regularized, embodiment that makes use of the first/second sets of measurements, a value for the left ventricular compliance $\kappa$ could be calculated using the following equation:

$$\kappa = \frac{E\left(\frac{\partial V}{\partial t}(t)\right)}{E\left(\frac{\partial P}{\partial t}(t)\right)} \quad (5)$$

It has previously been explained how the first/second set of measurements may be measurements representing a particular period of time (e.g. are all within a predetermined phase of the subject's heart, such as the diastolic phase or the end of the diastolic phase).

To reduce the effect of noise, it is preferable for the time period to be selected so that the denominator (of equation (3) or (5), or any other equation for calculating left ventricular compliance $\kappa$ that makes use of a ratio) is large.

This could be achieved by selecting the time period represented by the first/second set of measurements to contain a point in time $t_1$ at which the function in the denominator is at a maximum (with respect to all known points in time, e.g. within a particular cardiac cycle of the subject's heart). Thus, referencing equation (3) by example only, the time period represented by the first/second set of measurements should contain a time $t_1$ for which the value of $$\left|\frac{\partial P}{\partial t}(t_1)\right|^2$$

is greater than the value of $$\left|\frac{\partial P}{\partial t}(t)\right|^2$$

for any other value of t (e.g. within the same cardiac cycle of the subject's heart). The time period represented by the first/second set of measurements may be centered around this point in time $t_1$, e.g. to represent a predetermined fraction of the cardiac cycle.

A plurality of values for the left ventricular compliance $\kappa$ could be generated for different versions of the first and second sets of measurement. Each version of the first and second sets of measurements may correspond to sets of measurements associated with different time period (e.g. different parts of the motion of the subject's heart).

In some examples, time periods associated with different versions of the first/second sets of measurements may represent a time period of a different cardiac cycle of a subject. In other examples, time periods associated with different versions of first/second sets of measurements may be a time period of a sliding window. Other approaches will be apparent to the skilled person.

The method 100 may further comprise a step 160 of controlling a user-perceptible output responsive to the left ventricular compliance estimated by the processing arrangement.

In particular, step 160 may comprise controlling the user-perceptible output to provide a visual representation of the (value(s) of the) left ventricular compliance calculated in step 150. This may be in the form of a numerical indicator (e.g. a visual representation of a number), a graphical indicator, a color indicator (e.g. different colors representing different magnitudes of the left ventricular compliance) and so on.

In some examples, step 160 may comprise controlling the user-perceptible output to provide a visual, audible and/or haptic output that is responsive to the left ventricular compliance. For instance, if a value of the left ventricular compliance breaches some predetermined threshold, a visual, audible and/or haptic alert may be generated and output. As another example, step 160 may comprise controlling the user-perceptible output to provide a user-perceptible output of the left ventricular compliance (e.g. a measure).

Step 160 is not essential. For instance, it will be appreciated that the left ventricular compliance could act as a valuable input or feature for other (automated) method of analyzing characteristics of the subject's heart. Thus, there is a strong clinical benefit for generating (one or more values of) left ventricular compliance, even without controlling a user interface to display the estimated left ventricular compliance.

Preferably, the velocity data comprises color M-mode ultrasound data at the mitral inflow during a diastolic phase of the cardiac cycle of the heart. This data can be obtained using 4-chamber view or 3-chamber view. The Doppler beam is preferably aligned with the main direction of the mitral flow. Color M-mode ultrasound data ensures adequate temporal sampling to resolve the temporal derivative component in the Navier-Stokes equation.

In the foregoing examples, it is assumed that the pressure in the left atrium is effectively constant (i.e. has negligible variation). This assumption means that the calculated temporal variation in left ventricular pressure (e.g. using the Navier-Stokes equation previously described) is accurate.

However, for improved accuracy of the calculated left ventricular pressure, it is possible to modify the calculated temporal variation in left ventricular pressure (dP/dt) based on a temporal variation in left atrium pressure ($dP_a/dt$). Thus, in any foregoing equation, the value (dP/dt) may be replaced by the value ($dP'/dt=dP/dt+dP_a/dt$). The temporal variation in left atrium pressure can be calculated using the ultrasound data. In some examples, this can be obtained from a left atrium pressure monitor, e.g. positioned in the subject. In some examples, a pulmonary capillary wedge pressure can be used to represent the left atrium pressure, as the two are correlated with or proportional to one another. Thus, the left atrium pressure may be obtained from a pulmonary capillary wedge pressure monitor/sensor. Use of pulmonary capillary wedge pressure is less invasive, as it can be acquired with venous access, reducing a risk to the subject.

Figure 2:
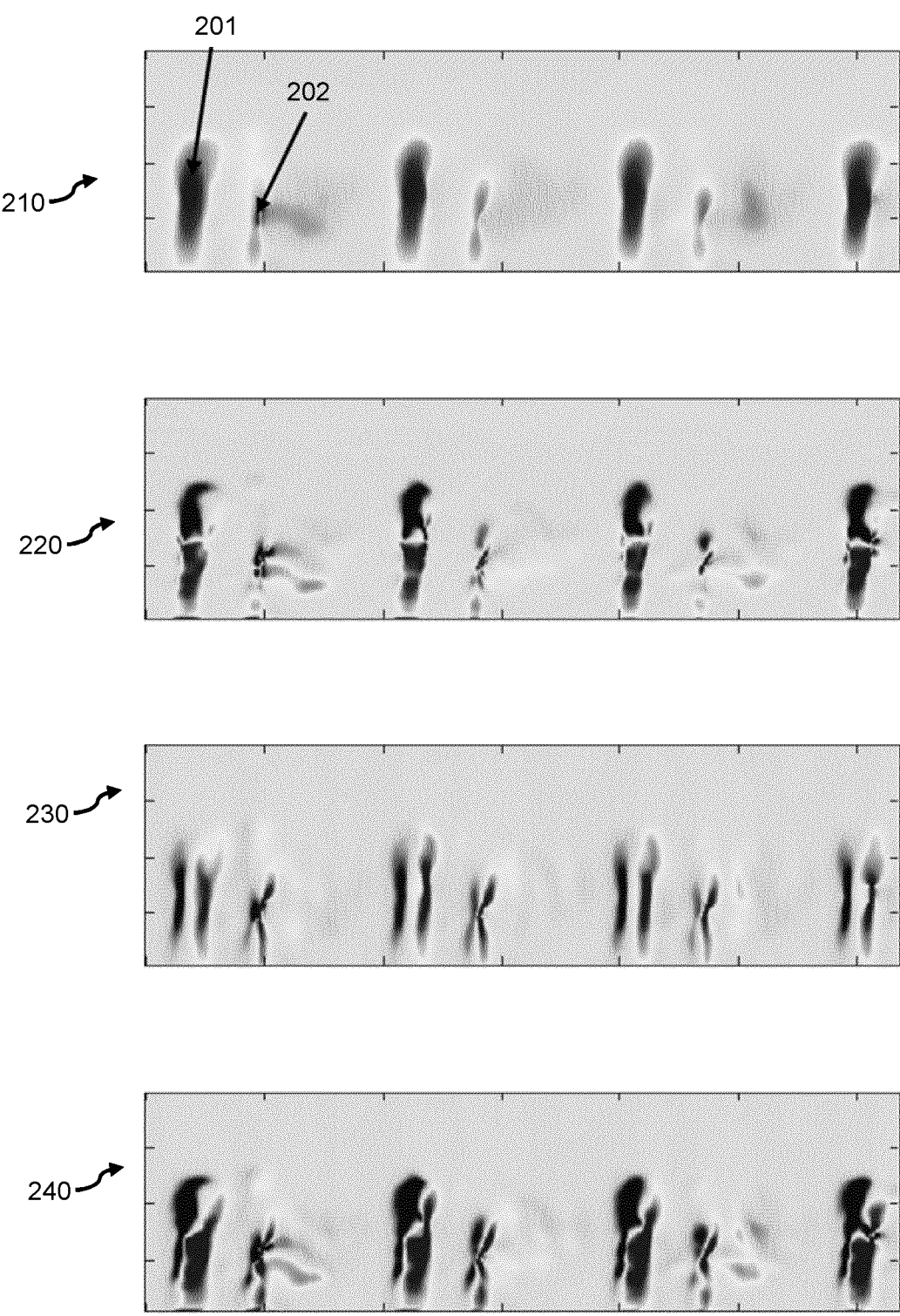
FIG. 2 provides a visual representation of functions derived from ultrasound data.

FIG. 2 provides various representations of partly processed velocity M-mode ultrasound data. In each visual representation, the E diastolic filling waves 201 and the A diastolic filling waves 202 can be identified. Each visual representation represents information captured over a period of time that encompasses three and a half heart cycles.

A first visual representation 210 represents velocity M-mode at the mitral valve after performing some post-processing including smoothing and dealiasing. This effectively represents an example of velocity data (of ultrasound data obtained in step 110 of FIG. 1).

The first visual representation 210 effectively provides a visual representation of the blood velocity function $v_r(r,t)$, where the x-axis represents time t, the y-axis represents distance r (in a direction along the mitral valve), and the saturation/greyscale value represents the (blood) velocity $v_r$.

The second visual representation 220 represents a convective component of the velocity M-mode ultrasound data. In this representation, the saturation/greyscale value instead represents the convective component $$-\rho v_r \frac{\partial v_r}{\partial r}$$

(rather than the blood velocity). The convective component is calculated through appropriate processing of the blood velocity function.

The third visual representation 230 represents an inertial component of the velocity M-mode ultrasound data. In this representation, the saturation/greyscale value instead represents the inertial component $$\left(-\rho \frac{\partial v_r}{\partial t}\right),$$

which is calculated through appropriate processing of the blood velocity function.

The fourth visual representation 240 represent a pressure gradient, i.e. the output of the Navier-Stokes equation, which is determined using the convective component and the inertial component. As previously explained, the pressure gradient can be integrated to get an estimate of left ventricular pressure.

Figure 3:
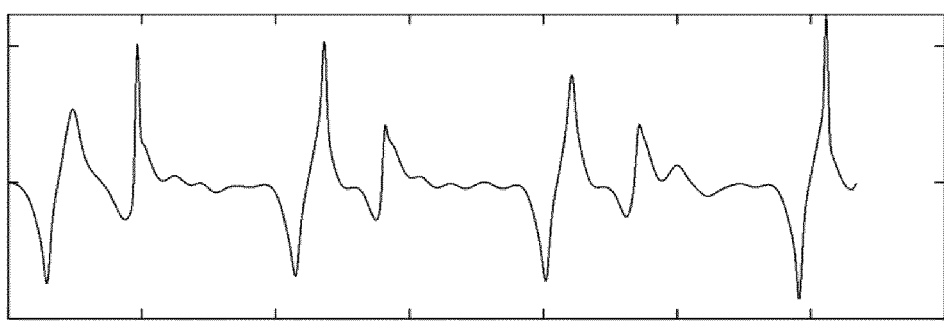
FIG. 3 is a graphical illustration of a function of left ventricular pressure.

FIG. 3 provides a representation of the integrated pressure gradient, i.e. a function of left ventricular pressure over time. The y-axis represents a relative pressure and the x-axis represent time. Approaches for generating the function of left ventricular pressure have been previously described.

Figure 4:
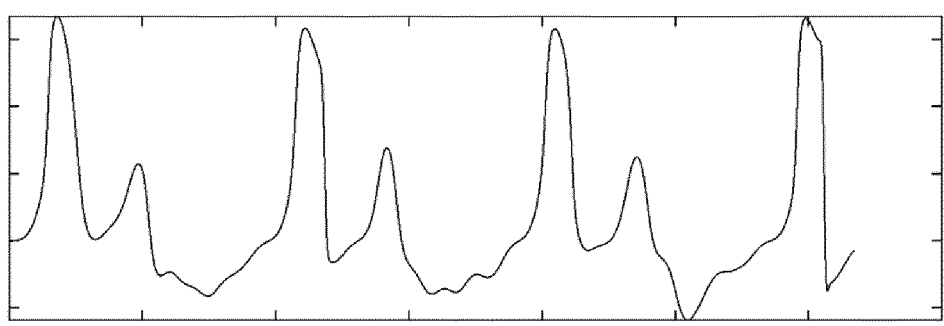
FIG. 4 is a graphical illustration of a function of the time derivative of left ventricular volume.

FIG. 4 provides a representation of blood velocity at the mitral valve. This may effectively be a slice of the first visual representation 210, i.e. for a value of r that identifies a location of the mitral valve. The blood velocity at the mitral valve can be used to calculate or represent the temporal variation of the left ventricular volume ($\partial V/dt$).

The skilled person would be readily capable of developing a processing arrangement for carrying out any herein described method. Thus, each step of any herein illustrated flow chart may represent a different action performed by a processing system, and may be performed by a respective module of the processing system.

Embodiments may therefore make use of a processing system. The processing arrangement can be implemented in numerous ways, with software and/or hardware, to perform the various functions required. A processor is one example of a processing arrangement which employs one or more microprocessors that may be programmed using software (e.g., microcode) to perform the required functions. A processing arrangement may however be implemented with or without employing a processor, and also may be implemented as a combination of dedicated hardware to perform some functions and a processor (e.g., one or more programmed microprocessors and associated circuitry) to perform other functions.

Examples of processing arrangement components that may be employed in various embodiments of the present disclosure include, but are not limited to, conventional microprocessors, application specific integrated circuits (ASICs), and field-programmable gate arrays (FPGAs).

In various implementations, a processor or processing arrangement may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing arrangement or may be transportable, such that the one or more programs stored thereon can be loaded into a processor or processing system.

13

Figure 5:
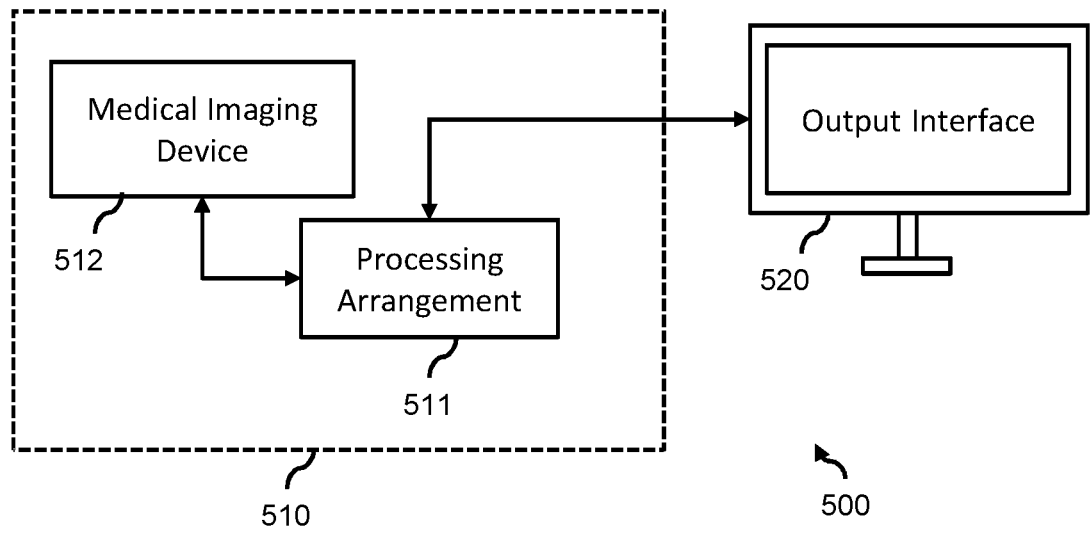
FIG. 5 illustrates a processing arrangement.

FIG. 5 illustrates a processing system 500 comprising an imaging system 510 and an output interface 520 according to an embodiment. The imaging system is itself an embodiment of the invention.

The imaging system 510 comprises a processing arrangement 511 and an ultrasound system 512. The processing arrangement 511, itself an embodiment of the invention, is configured to carry out any previously described method. Suitable examples of a processing arrangement have been previously described.

The ultrasound system 512 configured to capture ultrasound data of the subject's heart and provide the ultrasound data to the processing arrangement.

The output interface 520 is configured to provide a user-perceptible output responsive to the left ventricular compliance estimated by the processing arrangement. The operation of the output interface may be controlled by the processing arrangement 511, e.g. by carrying out step 160 described with reference to FIG. 1.

It will be understood that disclosed methods are preferably computer-implemented methods. As such, there is also proposed the concept of a computer program comprising code means for implementing any described method when said program is run on a processing system, such as a computer. Thus, different portions, lines or blocks of code of a computer program according to an embodiment may be executed by a processing arrangement or computer to perform any herein described method. In some alternative implementations, the functions noted in the block diagram(s) or flow chart(s) may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method for performing non-invasive estimation of left ventricular compliance for a subject, the computer-implemented method comprising:

obtaining ultrasound data of the subject's heart, wherein the ultrasound data was captured over a time period comprising at least a portion of a cardiac cycle of the heart and comprises color M-mode ultrasound data along a direction of mitral inflow;

determining, by processing the color M-mode ultrasound data, a velocity component along the direction of mitral inflow of the heart over the time period;

14 determining a temporal variation of the left ventricular pressure from the determined velocity component by processing the velocity component using a physical model;

determining, by processing the color M-mode ultrasound data of the obtained ultrasound data, a temporal variation of a left atrial pressure;

modifying the determined temporal variation of the left ventricular pressure based on the determined temporal variation of the left atrial pressure;

determining, by processing the obtained ultrasound data, a temporal variation of the left ventricle volume;

estimating the left ventricular compliance by processing the determined temporal variation of the left ventricle volume and the modified temporal variation of the left ventricular pressure; and determining, based on the left ventricular compliance, an indicator of likelihood of diastolic heart failure.

2. The computer-implemented method of claim 1, wherein the step of estimating the left ventricular compliance comprises determining the ratio between the temporal variation of the left ventricle volume and the temporal variation of the left ventricular pressure.

3. The computer-implemented method of claim 1, wherein the step of determining the temporal variation of the left ventricular pressure comprises processing the velocity component using the Navier-Stokes equation to determine the temporal variation of the left ventricular pressures.

4. The computer-implemented method of claim 1, wherein the step of determining the temporal variation of the left ventricle volume comprises determining the temporal variation of the left ventricle volume by processing the velocity component.

5. The computer-implemented method of claim 4, wherein the step of determining the temporal variation of the left ventricle volume comprises multiplying the velocity component by a surface area value, the surface area value representing a surface area size of the mitral annulus of the subject's heart.

6. The computer-implemented method of claim 5, further comprising a step of determining the surface area value, said step comprising:

determining, by processing the ultrasound data, a first volume of the left ventricle, of the subject's heart wherein the first volume is a volume of the left ventricle of the subject's heart at a first point during the portion of the cardiac cycle of the subject's heart;

determining, by processing the ultrasound data, a second volume of the left ventricle, of the subject's heart wherein the second volume is a volume of the left ventricle of the subject's heart at a second, later point during the portion of the cardiac cycle of the subject's heart;

determining the difference between the second volume and the first volume;

determining the integral of the velocity component between the first point and the second point during the portion of the cardiac cycle of the subject's heart; and determining the ratio between the difference between the second volume and the first volume and the integral, to thereby calculate the surface area value.

7. The computer-implemented method of claim 6, wherein:

the ultrasound data was captured over a time period comprising at least a portion of a cardiac cycle of the heart that includes an end-systolic phase of the cardiac cycle and an end-diastolic phase of the cardiac cycle, the first point is a point in the end-systolic phase of the cardiac cycle; and the second point is a point in the end-diastolic phase of the cardiac cycle.

8. The computer-implemented method of claim 5, wherein the surface area value is predetermined.

9. The computer-implemented method of claim 1, wherein:

the ultrasound data was captured over a time period comprising at least a portion of a cardiac cycle of the heart that includes an end-diastolic phase of the cardiac cycle;

the temporal variation of the left ventricle volume is a temporal variation of the left ventricle volume during the end-diastolic phase of the cardiac cycle; and the temporal variation of the left ventricular pressure is a temporal variation of the left ventricular pressure during the end-diastolic phase of the cardiac cycle.

10. The computer-implemented method of claim 1, wherein:

the step of determining a temporal variation of the left ventricle volume comprises processing the ultrasound data to determine a first set of measurements, each measurement in the first set of measurements representing the temporal variation of the left ventricle volume at a different, respective time point during the time period over which the ultrasound data was captured;

the step of determining a temporal variation of the left ventricular pressure comprises processing the at least one velocity component using a physical model to determine a second set of measurements, each measurement in the second set of measurements corresponding to a measurement of the first set of measurements and representing the temporal variation of the left ventricular pressure at the same time point as the corresponding measurement of the first set of measurements; and the step of estimating the left ventricular compliance comprises processing the first set of measurements and the second set of measurements to estimate the left ventricular compliance.

11. The computer-implemented method of claim 10, wherein the step of estimating the left ventricular compliance comprises:

multiplying each measurement of the first set of measurements by the corresponding measurement in the second set of measurements, to produce a multiplied set of measurements;

averaging the multiplied set of measurements to produce an averaged multiplied measurement;

squaring each measurement of the second set of measurements to produce a squared set of measurements;

averaging the squared set of measurements to produce an averaged squared measurement; and estimating the left ventricular compliance by determining a ratio between the averaged multiplied measurement and the averaged squared measurement.

12. A computer program product comprising computer program code means which, when executed on a computing device having a processing system, cause the processing system to perform a method comprising:

obtaining ultrasound data of a subject's heart, wherein the ultrasound data was captured over a time period comprising at least a portion of a cardiac cycle of the heart and comprises color M-mode ultrasound data along a direction of mitral inflow;

determining, by processing the color M-mode ultrasound data, a velocity component along the direction of mitral inflow of the heart over the time period;

determining a temporal variation of the left ventricular pressure from the determined velocity component by processing the velocity component using a physical model;

determining, by processing the color M-mode ultrasound data of the obtained ultrasound data, a temporal variation of a left atrial pressure;

modifying the determined temporal variation of the left ventricular pressure based on the determined temporal variation of the left atrial pressure;

determining, by processing the obtained ultrasound data, a temporal variation of the left ventricle volume;

estimating the left ventricular compliance by processing the determined temporal variation of the left ventricle volume and the modified temporal variation of the left ventricular pressure; and determining, based on the left ventricular compliance, an indicator of likelihood of diastolic heart failure.

13. A processing arrangement for performing estimation of left ventricular compliance for a subject, the processing arrangement being configured to:

obtain ultrasound data of the subject's heart, wherein the ultrasound data was captured over a time period comprising at least a portion of a cardiac cycle of the heart and comprises color M-mode ultrasound data along a direction of mitral inflow;

determine, by processing the color M-mode ultrasound data, a velocity component along the direction of mitral inflow of the heart over the time period;

determine a temporal variation of the left ventricular pressure from the determined velocity component by processing the velocity component using a physical model;

determine, by processing the color M-mode ultrasound data of the obtained ultrasound data, a temporal variation of a left atrial pressure;

modify the determined temporal variation of the left ventricular pressure based on the determined temporal variation of the left atrial pressure;

determine, by processing the obtained ultrasound data, a temporal variation of the left ventricle volume;

estimate the left ventricular compliance by processing the determined temporal variation of the left ventricle volume and the modified temporal variation of the left ventricular pressure; and determine, based on the left ventricular compliance, an indicator of likelihood of diastolic heart failure.

14. An imaging system comprising:

the processing arrangement of claim 13; and an ultrasound system configured to capture ultrasound data of the subject's heart and provide the ultrasound data to the processing arrangement.

15. A processing system comprising:

the processing arrangement of claim 13; and an output interface configured to provide a user-perceptible output responsive to the left ventricular compliance estimated by the processing arrangement.

* * * * *